US012734536B2

(12) United States Patent
Petit et al.

(10) Patent No.: US 12,734,536 B2
(45) Date of Patent: Sep. 15, 2026

(54) DEVICE FOR DISPENSING A FLUID PRODUCT AND METHOD FOR PRIMING SAME

(71) Applicant: APTAR FRANCE SAS, Le Neubourg (FR)

(72) Inventors: Ludovic Petit, Vitot (FR); Matthieu Savalle, Oissel (FR)

(73) Assignee: APTAR FRANCE SAS, Le Neubourg (FR)

( * ) Notice: Subject to any disclaimer, the term of this patent is extended or adjusted under 35 U.S.C. 154(b) by 225 days.

(21) Appl. No.: 18/833,959

(22) PCT Filed: Dec. 9, 2022

(86) PCT No.: PCT/FR2022/052304
§ 371 (c)(1),
(2) Date: Jul. 29, 2024

(87) PCT Pub. No.: WO2023/144468
PCT Pub. Date: Aug. 3, 2023

(65) Prior Publication Data

US 2026/0183780 A1 Jul. 2, 2026

(30) Foreign Application Priority Data

Jan. 31, 2022 (FR) ....................................... 2200837

(51) Int. Cl.
*B05B 11/10* (2023.01)
*A61M 11/00* (2006.01)
(Continued)

(52) U.S. Cl.
CPC ....... *B05B 11/1007* (2023.01); *A61M 11/007* (2014.02); *A61M 15/08* (2013.01);
(Continued)

(58) Field of Classification Search
CPC ........... B05B 11/1007; B05B 11/00444; B05B 11/1047; B05B 11/1077; B05B 11/105;
(Continued)

(56) References Cited

U.S. PATENT DOCUMENTS 8,292,131 B2 * 10/2012 Pruvot ................ B05B 11/1074 222/378
2008/0029544 A1 * 2/2008 Margheritis ......... A61M 11/007 222/153.13

(Continued)

FOREIGN PATENT DOCUMENTS

DE 202 18 974 U1 7/2003
WO WO-2007138084 A2 * 12/2007 ......... B05B 11/1004

OTHER PUBLICATIONS

International Preliminary Report on Patentability dated Aug. 6, 2024 with a Translation of the Written Opinion of the International Searching Authority in Application No. PCT/FR2022/052304.

(Continued)

*Primary Examiner* — Paul R Durand
*Assistant Examiner* — Michael J. Melaragno
(74) *Attorney, Agent, or Firm* — Sughrue Mion, PLLC

(57) ABSTRACT

A device comprising a dispenser assembled on a container, the dispenser having a body containing a chamber, and a head having a port, said port having a stopper movable and/or deformable between a closed position and an open position. The head is axially movable between a rest position and an actuated position, a piston rigidly connected to the head being suitable for sliding in the chamber between a rest position and an actuated position. The chamber has three openings, a first opening connecting the chamber to the container when the piston is in its rest position, a second opening connecting the chamber to the port, and a third opening, the first and third openings being isolated from the chamber when the piston moves out of its rest position. The (Continued)

chamber is filled through the first opening when the dispenser is assembled on the container.

20 Claims, 5 Drawing Sheets

(51) Int. Cl.
*A61M 15/08* (2006.01)
*B05B 11/00* (2023.01)

(52) U.S. Cl.
CPC .... *B05B 11/00444* (2018.08); *B05B 11/0067* (2013.01); *B05B 11/1047* (2023.01); *B05B 11/105* (2023.01); *B05B 11/1059* (2023.01); *B05B 11/1074* (2023.01); *B05B 11/1077* (2023.01); *A61M 2207/00* (2013.01)

(58) Field of Classification Search
CPC ............. B05B 11/1059; B05B 11/1074; B05B 11/0067; A61M 11/007; A61M 15/08; A61M 2207/00
USPC .......................................................... 222/309
See application file for complete search history.

(56) References Cited

U.S. PATENT DOCUMENTS

2008/0149098 A1 6/2008 Bonney et al.
2010/0032499 A1 2/2010 Petit
2013/0221035 A1* 8/2013 Fourment ............... B29C 65/08 156/60
2014/0001213 A1* 1/2014 Petit .................... B05B 11/1001 222/321.6
2017/0259285 A1* 9/2017 Petit .................. A61M 5/31591
2020/0197630 A1* 6/2020 Petit .................... A61M 15/003
2023/0390506 A1* 12/2023 Graine ................. A61M 11/007
2024/0216935 A1* 7/2024 Perignon ............. B05B 11/0054
2024/0408324 A1* 12/2024 Savalle ................ A61M 11/007
2024/0424510 A1* 12/2024 Petit .................... B05B 11/0032
2025/0074691 A1* 3/2025 Le Faou ................ B65D 83/52
2025/0303429 A1* 10/2025 Petit .................... B05B 11/1008

OTHER PUBLICATIONS

International Search Report for PCT/FR2022/052304 dated Mar. 16, 2023.

* cited by examiner

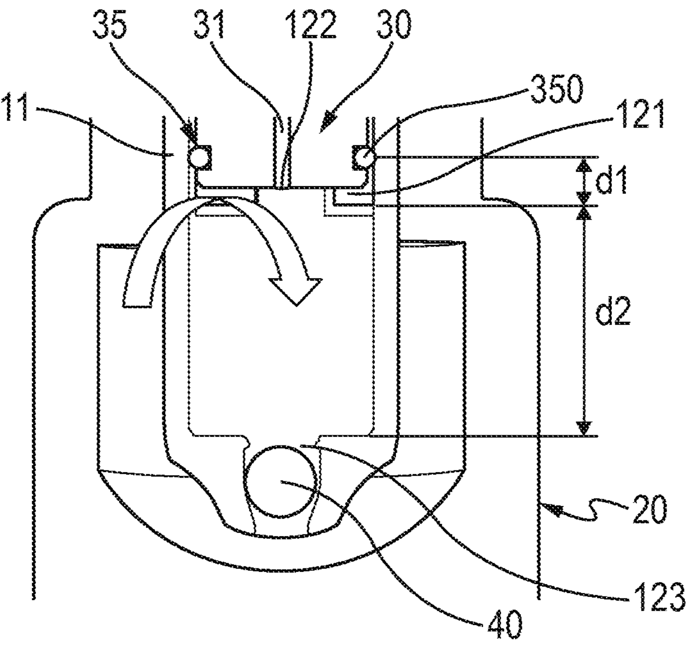
Fig. 5
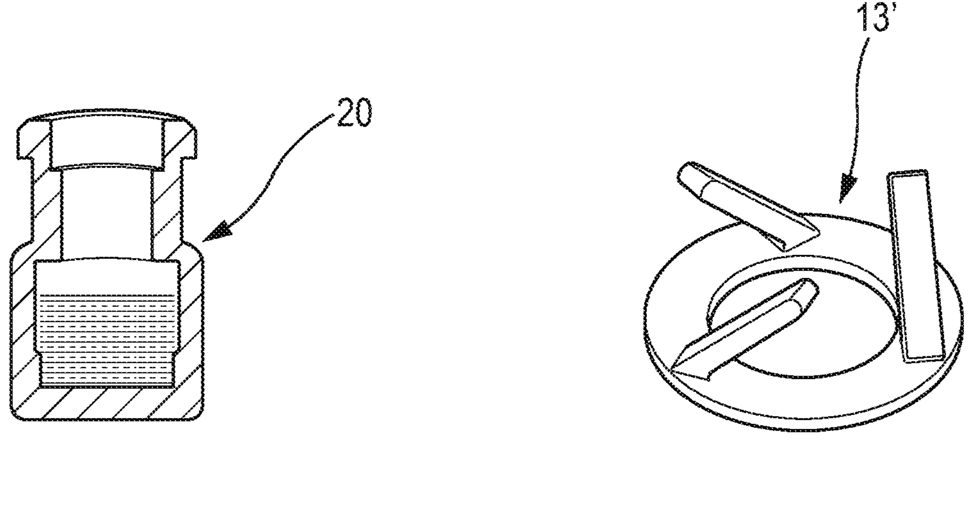
Fig. 6
Fig. 7

39
16
50
15
151
38
32
153
152
13
10
100
60
5
35
30
11
31
20
12
40

70
300

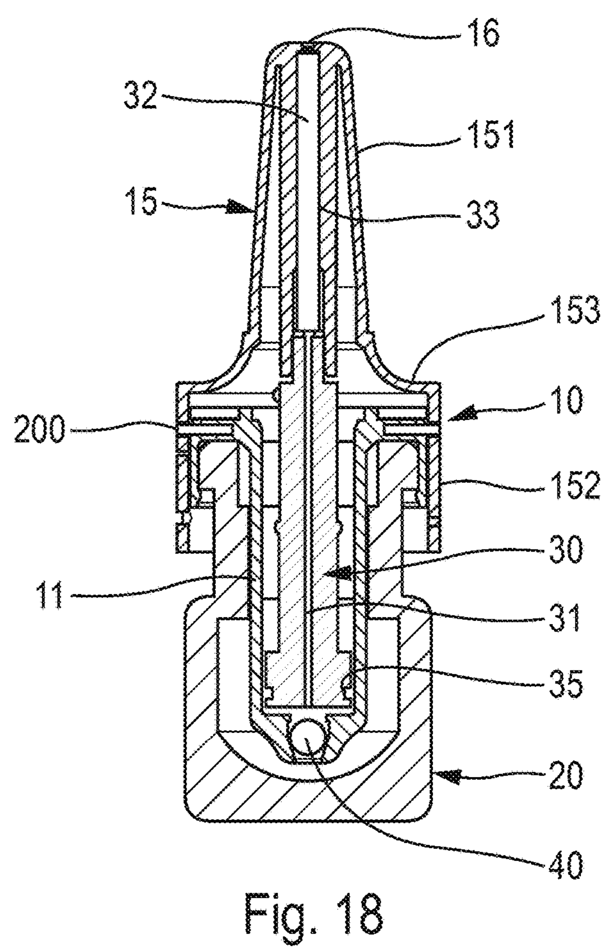
Fig. 18
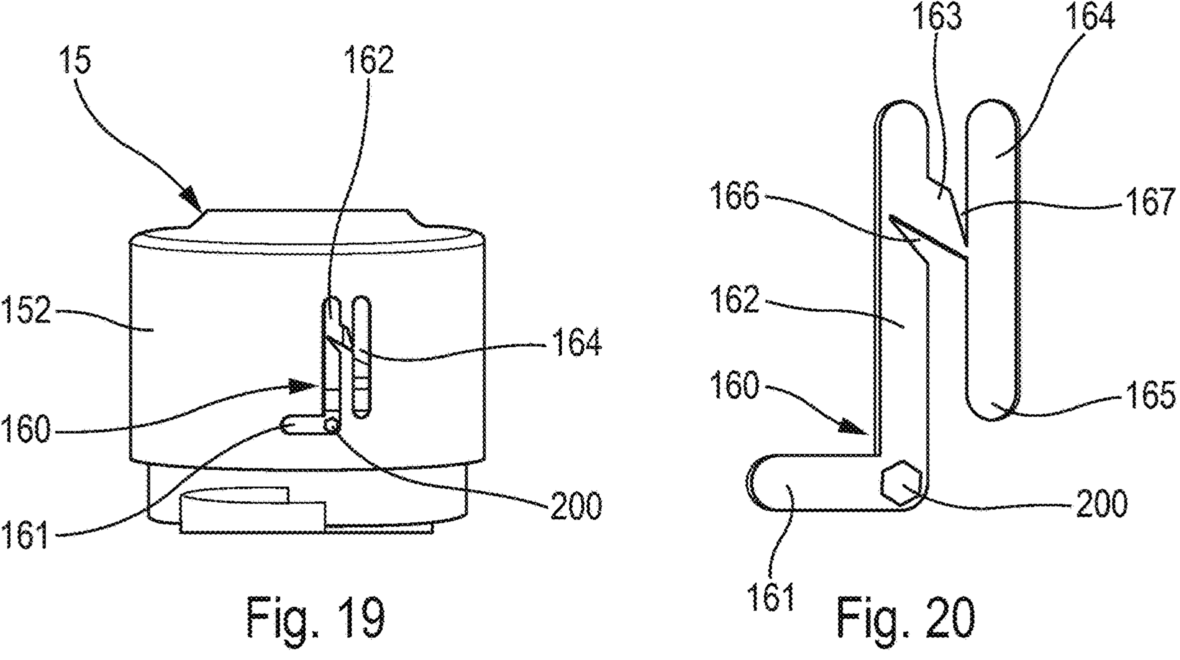
Fig. 19
Fig. 20

DEVICE FOR DISPENSING A FLUID PRODUCT AND METHOD FOR PRIMING SAME

CROSS REFERENCE TO RELATED APPLICATIONS

This application is a National Stage of International Application No. PCT/FR2022/052304 filed Dec. 9, 2022, claiming priority based on French Patent Application No. 2200837 filed Jan. 31, 2022.

The present invention relates to a device for dispensing a fluid product, in particular for a nasal delivery of one or two doses of a pharmaceutical fluid product. The present invention also relates to a method for priming a device for dispensing a fluid product.

A disadvantage of certain devices for a nasal delivery of fluid product, in particular those using a pump with a dosing chamber to define the volume of the dose dispensed upon each actuation, relates to the obligation to prime the pump to replace the air contained initially in the dosing chamber with fluid. This priming is generally done by one or more actuations of the device, consequently with a possible loss of fluid product.

The present invention aims to provide a device for dispensing a fluid product and a method for priming same, which do not have the abovementioned disadvantages.

More specifically, the present invention aims to provide such a device and method which require no priming of the pump.

The present invention also aims to provide such a device and method which are simple and inexpensive to manufacture and to assemble.

The present invention therefore relates to a device for dispensing a fluid product comprising a dispenser assembled on a reservoir containing fluid product, said reservoir containing several doses of fluid product dispensed in several successive actuations, said dispenser comprising a pump body containing a dosing chamber, and a dispensing head comprising a dispensing aperture, said dispensing aperture comprising a stopper that is movable and/or deformable between a closed position and an open position, said stopper being resiliently biased towards its closed position and being adapted to open during actuation, said dispensing head being axially movable with respect to said pump body between a rest position and an actuation position, a piston, secured to said dispensing head, being adapted to slide in said dosing chamber between a rest position and an actuation position, characterised in that said dosing chamber comprises three openings, a first opening connecting said dosing chamber to said reservoir when said piston is in the rest position prior to the first actuation, a second opening connecting said dosing chamber to said dispensing aperture and a third opening provided at the lower axial end of said pump body, said first and third openings being isolated from said dosing chamber when said piston moves out of its rest position, said dosing chamber being filled through said first opening when said dispenser is assembled on said reservoir.

Advantageously, said first opening is made in the cylindrical portion of said pump body in which the piston slides during actuation.

Advantageously, a lower edge of said first opening is disposed at rest at a distance d1 from the piston, such that, during actuation, said first opening is closed after an initial stroke corresponding to said distance d1.

Advantageously, said distance d1 forms less than 30% of the total actuation stroke of the piston, preferably around 20%.

Advantageously, said first opening comprises one or more slots formed in the cylindrical portion of said pump body.

Advantageously, wherein a hollow rod is disposed in said dispensing head, said hollow rod defining an expulsion channel connecting, during actuation, said dosing chamber to said dispensing aperture, said hollow rod comprising said piston.

Advantageously, wherein said piston is formed by a gasket, in particular an O-ring, assembled on said hollow rod.

Advantageously, said third opening comprises a stopper member, such as a ball, forming an inlet valve for said dosing chamber for filling it after each actuation.

Advantageously, the device includes a filtering membrane to filter the vent air after each actuation.

Advantageously, the device includes anti-actuation means for preventing axial displacement of said dispensing head relative to said pump body.

According to a first advantageous variant, said anti-actuation means comprise a removable clip arranged around said dispenser before the first actuation.

According to a second advantageous variant, said anti-actuation means comprise a radial projection secured to said pump body co-operating with a horizontal groove of a groove profile secured to said dispensing head.

Advantageously, the device includes actuation stroke limitation means for reducing the actuation stroke of said piston after the first dose has been dispensed by axially shifting the rest position of said piston after the first actuation.

In a first advantageous variant, said actuating stroke limiting means comprise a radial lip secured to said pump body co-operating with a radial shoulder secured to said piston.

According to a second advantageous variant, said of of actuating stroke actuation means comprise a radial projection secured to said pump body co-operating with a groove profile secured to said dispensing head.

Advantageously, said groove profile comprises a first vertical groove and a second parallel vertical groove, connected by an oblique groove, the rest position of said piston before the first actuation corresponding to said radial projection disposed in the lower axial end of said first vertical groove and the rest position of said piston after the first actuation corresponding to said radial projection disposed in the lower axial end of said second vertical groove, said lower axial ends being axially offset from one another.

Advantageously, said first vertical groove comprises a deformable wall portion adapted to guide said radial projection towards said oblique groove when said piston returns towards its rest position after the first dose has been dispensed.

Advantageously, said oblique groove comprises a second deformable wall portion suitable for preventing said radial projection from returning into said oblique groove when said radial projection has entered said second vertical groove.

Advantageously, said reservoir contains two doses of fluid product dispensed in two successive actuations.

The present invention also aims for a method for priming a device for dispensing fluid product, comprising the following steps:

- providing a reservoir which contains at least two doses of fluid product;

providing a dispenser comprising a pump body containing a dosing chamber, and a dispensing head comprising a dispensing aperture, said dispensing aperture comprising a stopper that is movable and/or deformable between a closed position and an open position, said stopper being resiliently biased towards its closed position and being adapted to open during actuation, said dispensing head being axially movable with respect to said pump body between a rest position and an actuation position, a piston, secured to said dispensing head, being adapted to slide in said dosing chamber between a rest position and an actuation position, said dosing chamber comprising three openings, a first opening connecting said dosing chamber to said reservoir when said piston is in the rest position prior to the first actuation, a second opening connecting said dosing chamber to said dispensing aperture and a third opening provided at the lower axial end of said pump body, said first and third openings being isolated from said dosing chamber when said piston moves out of its rest position, said dosing chamber being filled through said first opening when said dispenser is assembled on said reservoir, said method comprising the step of assembling said dispenser on said reservoir, by inserting said pump body in said reservoir with said piston in the rest position, this insertion moving the fluid product contained in said reservoir, said moved fluid product penetrating inside said dosing chamber through said first opening, to thus prime the device.

These features and advantages and others of the present invention will appear more clearly during the following detailed description, made in reference to the accompanying drawings, given as non-limiting examples, and in which:

FIG. 1 is a schematic, cross-sectional view of a device for dispensing a fluid product according to an advantageous first embodiment, during the joining of the dispenser to the reservoir, FIG. 2 is a view similar to that of FIG. 1, during the first actuation, FIG. 3 is a view similar to that of FIG. 2, after the first actuation, FIG. 4 is a view similar to that of FIG. 3, after loading the dosing chamber with another dose of fluid product;

FIG. 5 is an enlarged, schematic view of a portion of FIG. 1;

FIG. 6 is a schematic, cross-sectional view of a reservoir before joining of the dispenser, FIG. 7 is a schematic, perspective view of a plastic spring being able to replace the metal spring of FIGS. 1 to 4, FIG. 8 is a schematic, cross-sectional view of a device for dispensing a fluid product according to an advantageous second embodiment, after the joining of the dispenser to the reservoir, FIG. 9 is a view similar to that of FIG. 8, during the first actuation, FIG. 10 is a view similar to that of FIG. 9, after loading the dosing chamber with another dose of fluid product;

Figures 8, 9, 10, 11, 12, 13:
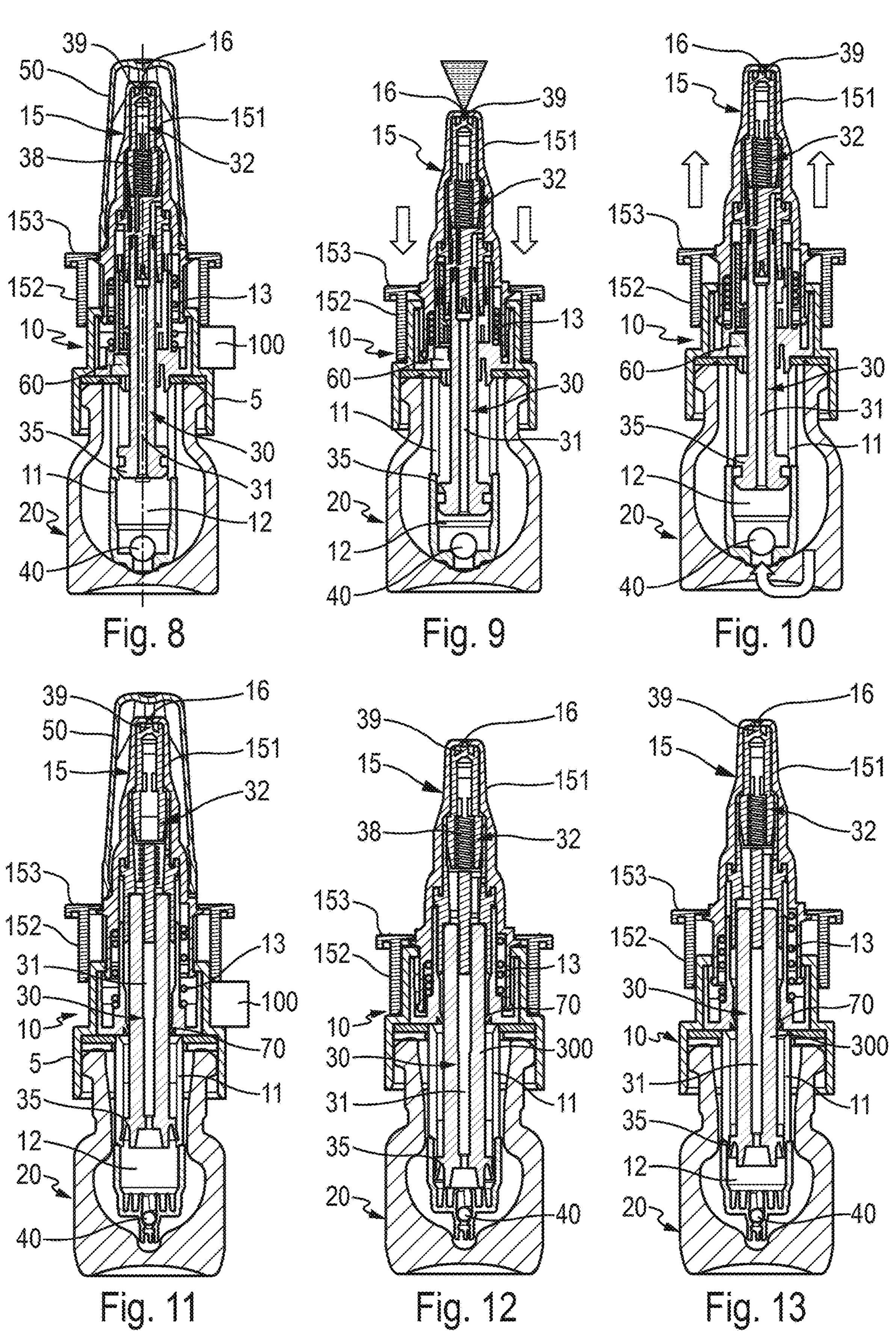
FIG. 11 is a schematic, cross-sectional view of a device for dispensing a fluid product according to an advantageous third embodiment, after the joining of the dispenser to the reservoir.
FIG. 12 is a view similar to that of FIG. 11, during the first actuation.
FIG. 13 is a view similar to that of FIG. 12, after loading the dosing chamber with another dose of fluid product.
Figure 15:
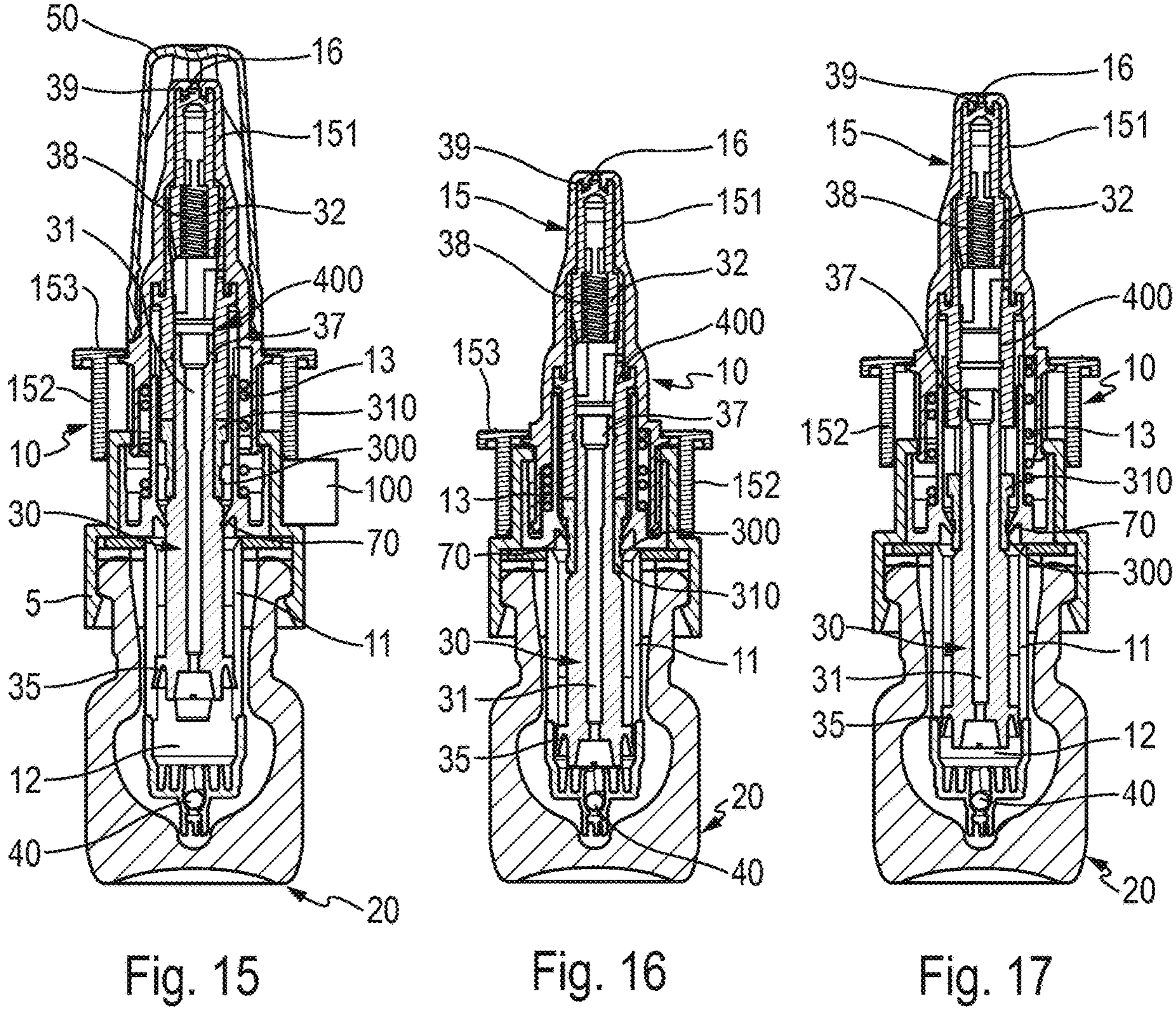

FIGS. 15 and 17 are views similar to the views in FIGS. 11 and 13, showing an advantageous variant embodiment of the third embodiment, FIG. 18 is a schematic cross-sectional view of a device for dispensing a fluid product according to a fourth advantageous embodiment, showing an alternative solution for performing the anti-actuation and dose volume modification functions after the first dose, in the actuated position, FIG. 19 is a schematic, detailed view of the fourth embodiment, and FIG. 20 is larger-scale view of a profile of FIG. 19.

The terms "axial" and "radial" are relative to the longitudinal central axis of the device. The terms "upstream" and "downstream" are relative to the direction of flow of the fluid during actuation. The terms "top" and "bottom" refer to the upright position of the device represented in FIGS. 1 to 4, 8 to 13, and 15 to 18.

In a first advantageous embodiment of FIGS. 1 to 5, a dispenser 10 is assembled to a reservoir 20 which contains the fluid product to be dispensed, typically a pharmaceutical-type liquid.

The reservoir 20 is advantageously formed by a hollow and blind body, comprising a single opening and which contains one or more dose(s) of fluid product to be dispensed. An example of an implementation of this reservoir 20 designed for the embodiment of FIGS. 1 to 5 is represented in an isolated manner in FIG. 6.

The present invention applies to a single-dose device which only contains a single dose of fluid product in the reservoir 20, but it is particularly designed for so-called two-dose devices, where the reservoir 20 contains two doses of fluid product, dispensed in two successive actuations. Optionally, the reservoir 20 could contain more than two doses, for example three or four doses.

The dispenser 10 comprises a pump body 11 which contains a dosing chamber 12, and a dispensing head 15 comprising a dispensing aperture 16, preferably oriented axially. The dispensing orifice 16 serves to dispense a dose of fluid out from said dispensing head 15 while the device is being actuated by a user. The dispensing head 15 is axially movable with respect to the pump body 11 between a rest position and an actuation position.

Figures 1, 2, 3, 4:
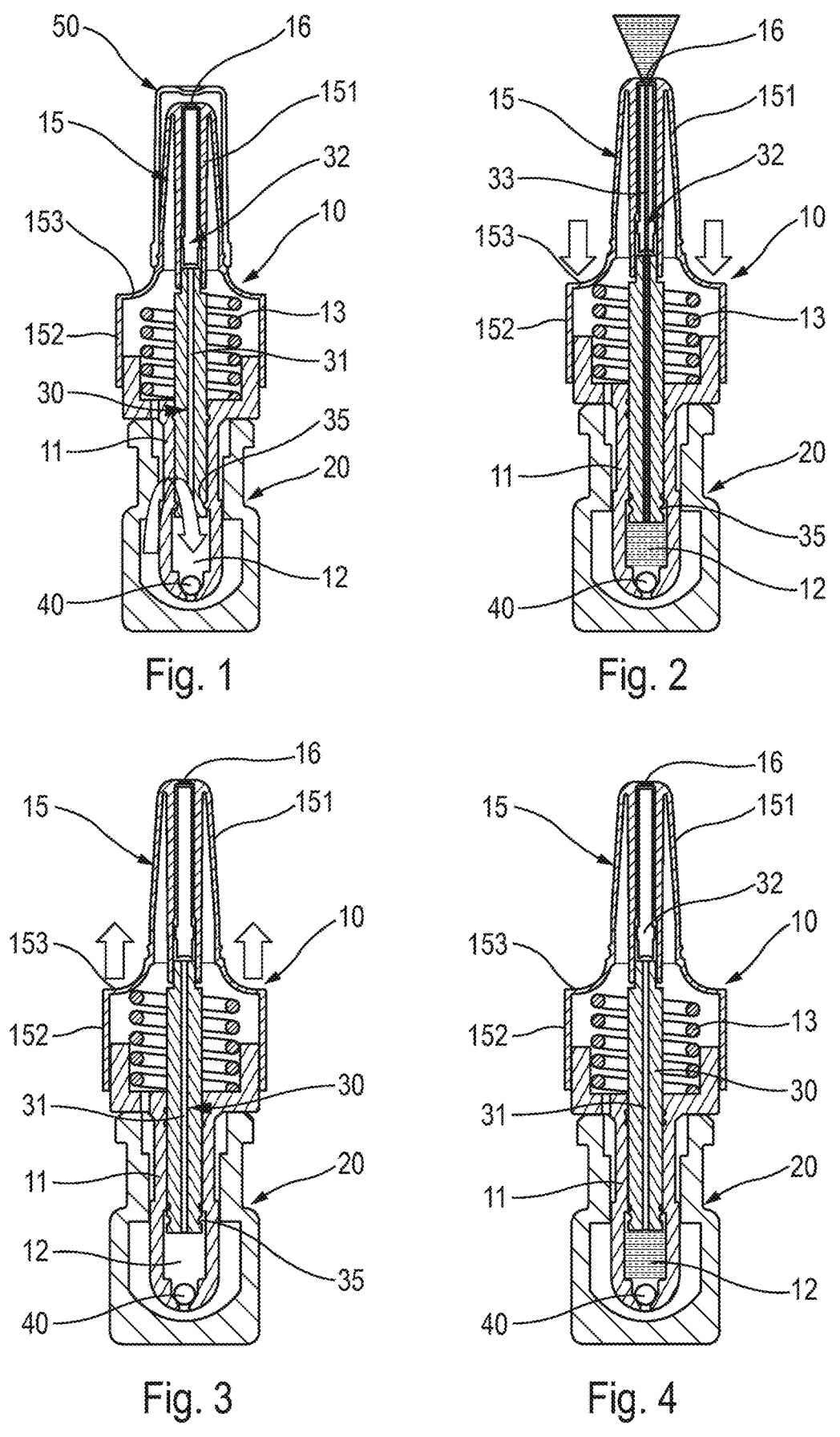

At rest, a removable protective cap 50 can be disposed on the dispensing head 15 to protect the dispensing aperture 16, as can be seen in FIGS. 1, 8 and 11.

A spring 13 is disposed between the pump body 11 and the dispensing head 15 to urge the latter to its rest position.

In the embodiments of FIGS. 1 to 4 and 8 to 17, the spring 13 is of the conventional coil type, generally metal.

In a variant, it can be considered to replace the spring 13 with a plastic elastically deformable element 13'. FIG. 7 shows an example of such an elastic element 13'.

The dispensing head 15 comprises an extended nasal endpiece 151 comprising, at its axial end, said dispensing aperture 16, as well as a side body 152, connected to said nasal endpiece 151 via an almost radial flange 153. Alternatively, as can be seen in FIGS. 8 to 17 of the second and third embodiments, the side body 152 and the flange 153 may be formed on a separate piece assembled on the dispensing head 15.

A hollow rod 30 is connected to the dispensing head 15, said hollow rod 30 defining an expulsion channel 31.

An insert 32, advantageously hollow, may be disposed in the dispensing head 15 in order to define, upstream from the dispensing aperture 16, an expulsion channel portion 33 of reduced radial dimension. This makes it possible not only to limit the dead volume, but also to achieve good spraying through the dispensing aperture 16.

Advantageously, a spray profile can be provided directly upstream of said dispensing aperture 16, between said insert 32 and the bottom wall of the dispensing head 15.

On the opposite side, the rod 30 comprises a piston 35 designed to slide in the dosing chamber 12 of the pump body 11 between a rest position and an actuation position. For example, a gasket 350, in particular an O-ring, may be assembled on the hollow rod 30 in order to form the piston, as can be seen more particularly in FIG. 5. In a variant, the piston 35 could be formed integrally with the hollow rod 30. Other known variants can also be envisaged for producing the piston 35.

The assembling of the dispenser 10 on the reservoir 20 can be done in any known manner, for example by using a fixing ring to fix the pump body 11 to a neck of the reservoir.

The dosing chamber 12 comprises at least two openings 121, 122, 123. These openings are distinct, and each have a specific function.

In the case of a single dose, when the reservoir 20 only contains a single dose of fluid product, there are two openings 121 and 122.

In the case of a two-dose or multidose device, when the reservoir 20 contains at least two doses of fluid product, there are three openings 121, 122 and 123.

The first opening 121 is made in the cylindrical portion of the pump body 11 in which the piston 35 slides during actuation.

This first opening 121 connects the dosing chamber 12 to the reservoir 20 when the piston 35 is in the rest position. During actuation, the piston 35 slides axially downwards in the pump body 11. Optionally, in particular in the case of a two-dose, after dispensing of the first dose, the piston 35 raises axially to return into its rest position. At the end of this return stroke, the first opening 121 is opened again.

As can be seen in FIG. 5, the first opening 121 is preferably disposed at rest in the proximity of the piston 35, such that after a small initial actuation stroke d1, illustrated in FIG. 5, the piston 35 extends beyond the first opening 121, and for the rest of the actuation stroke d2, this first opening 121 is therefore closed. In other words, a lower edge of the first opening 121 is disposed at rest at a distance d1 from the piston 35, such that, during actuation, said first opening 121 is closed after an initial stroke corresponding to said distance d1. Advantageously, the distance d1 forms less than 30% of the total actuation stroke d1+d2 of the piston 35, preferably around 20%.

Advantageously, the first opening 121 comprises one or more slots formed in the cylindrical portion of the pump body 11. The number of slots, which could also be holes, can be any number, for example one, two, three or four slots.

The second opening 122 is axial and is provided at the lower axial end of the hollow rod 30. The second opening 122 thus connects the dosing chamber 12 to the expulsion channel 31.

The third opening 123 is axial and is provided at the lower axial end of the pump body 11. This third opening is only provided if the device is a two-dose or a multidose device. A stopper member 40, such as a ball, is provided to close the third opening 123 from the start of actuation, and to open the third opening 123 from the start of the return stroke of the piston 35, when it returns from its actuation position to its rest position. This third opening 123 together with the stopper member 40 therefore forms a conventional inlet valve for the dosing chamber 12, for filling it after each actuation of the pump due to the depression generated by the piston 35 which raises to its rest position.

Figure 14:
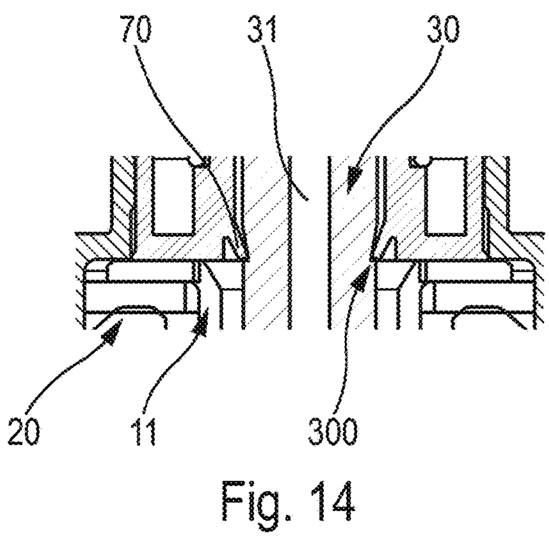
FIG. 14 is an enlarged, schematic view of a portion of FIG. 13.

In the example represented in the FIG. 14, the dosing chamber 12 does not comprise any outlet valve at the second opening 122, and the dispensing aperture 16 does not comprise any stopper forming an outlet valve. The dosing chamber 12 is therefore permanently connected to the atmosphere. However, the ratio of the areas of the cross-sections of the expulsion channel 31 and of the third opening 123 is such that the depression is generated even when in the dosing chamber 12 when the piston 35 returns to its rest position. Thus, for example, the diameter of the expulsion channel 31 can be of 0.3 mm, which gives an area of the cross-section of 0.7 $mm^2$, while the diameter of the third opening 123 is typically around 3 mm, which gives an area of the cross-section of 7 $mm^2$, that is a ratio of 1 to 100. However, in a variant, an outlet valve could be considered at the second opening 122 of the dosing chamber, or a stopper at the dispensing aperture 16, as in the second and third embodiments described below with reference to FIGS. 8 to 17.

Thus, the invention makes it possible to produce a device without priming.

During the assembling of the dispenser 10 to the reservoir 20, the dispensing head 15 and the piston 35 are in the rest position with respect to the pump body 11. The first opening 121 is therefore open. Thus, when the dispenser 10 is assembled to the reservoir 20, the pump body 11 penetrates inside the reservoir 20 and due to this, moves the fluid product contained in the reservoir 20. The volume of moved fluid product corresponds to the volume that the pump body 11 occupies in the reservoir after joining. The fluid product thus moved therefore penetrates inside the dosing chamber 12 via the first opening 121, as illustrated by the arrow in FIGS. 1 and 5. The assembling is done in the upright position, the dosing chamber 12 is filled up to the edge of the first opening 121, thus defining the dose to be dispensed. The pump is therefore primed from the assembling, and there is no need to perform priming actuations before using the device.

During the first actuation, the user places two fingers on the radial flange 153 formed on the dispensing head 15, and presses with the thumb on the bottom of the reservoir 20. During such an actuation, the reservoir 20 is therefore pushed axially in the direction of the dispensing aperture 16, such that the piston 35 slides in the dosing chamber 12. The first opening 121 is closed after the initial small stroke d1 and the third opening 123 is closed by the pressure exerted by the fluid product on the stopper member 40 forming a valve. The contents of the dosing chamber 12 is thus dispensed through the second opening 122 towards the dispensing aperture 16.

If the device is a two-dose or a multidose device, when the user releases the pressure on the dispensing head 15 after the first actuation, the spring 13 returns the piston 35 to its rest position. A depression is thus created in the dosing chamber 12, which opens the third opening 123 to fill the dosing chamber 12 from the reservoir 20 through this third opening 123.

The device is thus ready for a second actuation.

Thus, the first opening 121 ensures the transfer of the first dose into the dosing chamber 12 during the joining, and the third opening 123 ensures the transfer of the second dose (and optionally other additional doses) in the dosing chamber 12 after dispensing of the first dose.

FIGS. 8 to 10 show a second advantageous embodiment, in which a stopper 39 is provided at the dispensing aperture 16. The stopper 39 is axially movable and/or deformable so as to close the dispensing aperture 16 at rest and open the dispensing aperture 16 during actuation. This stopper 39 thus forms an outlet valve for the pump. A spring 38 can urge the stopper 39 towards its closed position, and during actuation, the pressure of the fluid product being expelled makes it possible to move and/or deform the stopper 39 towards its open position. The stopper 39 may for example be formed on the insert 32 arranged in the dispensing head 15 upstream from the dispensing aperture 16. Other stopper types can also be envisaged. In a variant, an outlet valve could also be provided in the dosing chamber to replace the stopper at the dispensing aperture.

In this second advantageous embodiment, a filtering membrane 60 is provided to filter the vent air that enters the pump after each actuation.

In addition, a removable anti-actuation clip 100 is advantageously arranged around the dispensing head 15 to prevent actuation during transportation and storage. In the example shown, the clip 100 is arranged between the lower edge of the side body 152 and the fixing ring 5 that fixes the pump body 11 on the reservoir 20.

FIGS. 11 to 14 show a third advantageous embodiment, also comprising a stopper 39 and a removable anti-actuation clip 100 as described above.

In this third embodiment, there is no filtering membrane, but it could also be applied here.

The third embodiment, which applies to a multi-dose, in particular a two-dose, comprises actuating stroke limitation means, for compensating from the second dose the volume of air contained in the expulsion channel 31 before the first actuation. Indeed, before the first actuation, the dosing chamber 12 is filled with fluid product during the assembly of the dispenser 10 on the reservoir 20, but there is still air between the dosing chamber 12 and the dispensing aperture 16, in particular in the expulsion channel 31. Thus, during the first actuation, the entire volume of the dosing chamber 12 is not expelled, since fluid product will remain in these parts that previously contained air, in particular the expulsion channel 31. Therefore, to ensure a constant expelled dose between the first dose and the second dose, provision is made to limit the actuation stroke of the piston 35 from the second dose. This also makes it possible to permanently isolate the first opening 121 of the dosing chamber 12 after the first actuation.

FIG. 14 illustrates in detail the solution of the third embodiment, in which the hollow rod 30 that supports the piston 35 comprises a radial shoulder 300, which, before the first actuation, is arranged axially above a radial lip 70 formed on a part secured to the pump body 11. During the first actuation, the shoulder 300 will pass below said lip 70, and when the piston returns to its rest position after the first actuation, the lip 70 will define the stop position of the piston at rest, which will therefore be axially offset downwards relative to its stop position at rest before the first actuation. Thus, from the second dose, the actuation stroke of the piston 35 will be reduced, which will compensate for the volume of fluid not dispensed during the first actuation due to the volume of air upstream of the dispensing aperture 16.

FIGS. 15 to 17 describe an advantageous variant of the third embodiment of FIGS. 11 to 14. In this variant, the stroke of the piston 35 from the second dose is decorrelated from the stroke of the dispensing head 15, so that even if the piston exerts a reduced actuation stroke from the second dose, the dispensing head 15 will still make the same actuation stroke as for the first dose. This is particularly advantageous in order not to modify the user's sensations between the first and second doses.

In this variant, the hollow rod 30 is axially movable relative to the dispensing head 15. In the example shown in FIGS. 15 to 17, the upper end 37 of the hollow rod slides axially in a hollow sleeve 400 secured to the dispensing head 15, preferably in a sealed manner.

Advantageously, the shoulder 300 is not necessarily formed directly on the hollow rod 30, but on a ring 310 arranged around said hollow rod 30.

Thus, when the piston returns to its rest position after the first dose has been dispensed, as can be seen in FIGS. 16 and 17, the radial lip 70 will cooperate with the shoulder 300 to modify the axial position of the rest position of the piston 35. On the other hand, the dispensing head 15 will be returned by the spring 13 to its initial rest position, with the upper end 37 of the hollow rod sliding axially in the hollow sleeve 400. When the user again actuates the device to dispense the second dose, the dispensing head 15 will first make a dead stroke, during which the upper end 37 of the hollow rod will slide axially in the hollow sleeve 400 in the other direction, then move the piston 35 over the end of its actuation stroke.

FIGS. 18 to 20 illustrate a fourth advantageous embodiment. This fourth embodiment does not include a stopper or a filtering membrane, but these elements could also be present here.

This fourth embodiment describes an alternative system for, on the one hand, carrying out the anti-actuation during transport and storage, and, on the other hand, carrying out the actuation stroke limitation.

As can be seen in detail in FIGS. 19 and 20, the lateral body 152 of the dispensing head 15 comprises at least one groove profile 160 co-operating with a radial projection 200 secured to the pump body 11. Advantageously, there may be two diametrically opposite groove profiles 160.

The advantageous groove profile 160 of FIGS. 19 and 20 comprises a horizontal groove 161, which is extended at one of its lateral ends by a first vertical groove 162. Thus, before the first actuation, the radial projection 200 is in said horizontal groove 161, on the lateral side opposite to the first vertical groove 162, and consequently, the axial movement of the dispensing head 15 with respect to the pump body 11 is prevented.

To be able to perform the first actuation, the user must turn the dispensing head 15, to slide the radial projection 200 towards the other lateral side of the horizontal groove 161, to find himself in front of the first vertical groove 162. It is the position shown in FIGS. 19 and 20.

The device can then be actuated to dispense the first dose.

During this first actuation stroke, the radial projection 200 rises to the top of the first vertical groove 162, passing over a deformable wall portion 166 projecting into the first vertical groove 162.

When the piston 35 returns to its rest position after the first actuation, the radial projection 200 is guided by said deformable wall portion 166 in an oblique groove 163 which leads towards a second vertical groove 164, parallel to the first vertical groove 162, but the lower axial end 165 of which is offset axially upwards relative to the lower axial end of the first vertical groove 162, formed by the bottom of the horizontal groove 161.

Thus, the rest position of the piston 35 after the first actuation is offset axially relative to that before the first actuation, and the second actuation, as well as any other actuations, will have a reduced actuation stroke, defined by the height of the second vertical groove 164, less than the height of the first vertical groove 162. Advantageously, a second deformable wall portion 167 is provided between the oblique groove 163 and the second vertical groove 164, to prevent the radial projection 200 from returning into the oblique groove 163 during the second actuation, or subsequent actuations. Typically, this second deformable wall portion 167, in its undeformed state, projects into the oblique groove 163 and aligns with the side wall of the second vertical groove 162.

Naturally, variants of embodiment can be considered, without deviating from the scope of the invention, such as defined by the accompanying claims.

The invention claimed is:

1. A device for dispensing a fluid product comprising a dispenser assembled on a reservoir containing fluid product, said reservoir containing several doses of fluid product dispensed in several successive actuations, said dispenser comprising a pump body containing a dosing chamber, and a dispensing head comprising a dispensing aperture, said dispensing aperture comprising a stopper that is movable and/or deformable between a closed position and an open position, said stopper being resiliently biased towards its closed position and being adapted to open during actuation, said dispensing head being axially movable with respect to said pump body between a rest position and an actuation position, a piston, secured to said dispensing head, being adapted to slide in said dosing chamber between a rest position and an actuation position, said dosing chamber comprises three openings, a first opening connecting said dosing chamber to said reservoir when said piston is in the rest position prior to the first actuation, a second opening connecting said dosing chamber to said dispensing aperture and a third opening provided at the lower axial end of said pump body, said first and third openings being isolated from said dosing chamber when said piston moves out of its rest position, said dosing chamber being filled through said first opening when said dispenser is assembled on said reservoir.

2. The device according to claim 1, wherein said first opening is made in the cylindrical portion of said pump body in which the piston slides during actuation.

3. The device according to claim 1, wherein a lower edge of said first opening is disposed at rest at a distance (d1) from said piston, such that during actuation, said first opening is closed after an initial stroke corresponding to said distance (d1).

4. The device according to claim 3, wherein said distance (d1) forms less than 30% of the total actuation stroke of said piston, preferably around 20%.

5. The device according to claim 1, wherein said first opening comprises one or more slots formed in the cylindrical portion of said pump body.

6. The device according to claim 1, wherein a hollow rod is disposed in said dispensing head, said hollow rod defining an expulsion channel connecting, during actuation, said dosing chamber to said dispensing aperture, said hollow rod comprising said plunger.

7. The device according to claim 6, wherein said piston is formed by a seal, in particular an O-ring, assembled to said hollow rod.

8. The device according to claim 1, wherein said third opening comprises a stopper member, such as a ball, forming an inlet valve for said dosing chamber for filling it after each actuation.

9. The device according to claim 1, comprising a filtering membrane for filtering the vent air after each actuation.

10. The device according to claim 1, comprising anti-actuation means for preventing the axial movement of said dispensing head relative to said pump body.

11. The device according to claim 10, wherein said anti-actuation means comprise a removable clip arranged around said dispenser before the first actuation.

12. The device according to claim 10, wherein said anti-actuation means comprise a radial projection secured to said pump body co-operating with a horizontal groove of a groove profile secured to said dispensing head.

13. The device according to claim 1, comprising actuation stroke limitation means for reducing the actuation stroke of said piston after the first dose has been dispensed by axially shifting the rest position of said piston after the first actuation.

14. The device according to claim 13, wherein said actuation stroke limitation means comprise a radial lip secured to said pump body co-operating with a radial shoulder secured to said piston.

15. The device according to claim 13, wherein said actuation stroke actuation means comprise a radial projection secured to said pump body co-operating with a groove profile secured to said dispensing head.

16. The device according to claim 15, wherein said groove profile comprises a first vertical groove and a second parallel vertical groove, connected by an oblique groove, the rest position of said piston before the first actuation corresponding to said radial projection disposed in the lower axial end of said first vertical groove and the rest position of said piston after the first actuation corresponding to said radial projection disposed in the lower axial end of said second vertical groove, said lower axial ends being axially offset from one another.

17. The device according to claim 16, wherein said first vertical groove comprises a deformable wall portion adapted to guide said radial projection towards said oblique groove when said piston returns towards its rest position after the first dose has been dispensed.

18. The device according to claim 15, wherein said oblique groove comprises a second deformable wall portion suitable for preventing said radial projection from returning into said oblique groove when said radial projection has entered said second vertical groove.

19. The device according to claim 1, wherein said vessel contains two doses of fluid product dispensed in two successive actuations.

20. A method for priming a device for dispensing a fluid product, comprising the following steps:

providing a reservoir which contains at least two doses of fluid product;

providing a dispenser comprising a pump body containing a dosing chamber, and a dispensing head comprising a dispensing aperture, said dispensing aperture comprising a stopper that is movable and/or deformable between a closed position and an open position, said stopper being resiliently biased towards its closed position and being adapted to open during actuation, said dispensing head being axially movable with respect to said pump body between a rest position and an actuation position, a piston, secured to said dispensing head, being adapted to slide in said dosing chamber between a rest position and an actuation position, said dosing chamber comprising three openings, a first opening connecting said dosing chamber to said reservoir when said piston is in the rest position prior to the first actuation, a second opening connecting said dosing chamber to said dispensing aperture and a third opening provided at the lower axial end of said pump body, said first and third openings being isolated from said dosing chamber when said piston moves out of its rest position, said method comprises the step of joining said dispenser to said reservoir, by inserting said pump body in said reservoir with said plunger in the rest position, this insertion moving the fluid product contained in said reservoir, said moved fluid product penetrating inside said dosing chamber through said first opening, to thus prime the device.

* * * * *